United States Patent
Melvin et al.

(10) Patent No.: US 6,582,375 B2
(45) Date of Patent: Jun. 24, 2003

(54) SYSTEM FOR STUDY OF GLOBAL UNI-OR BI-VENTRICULAR FUNCTION OF AN EXPLANTED, REPERFUSED HEART

(75) Inventors: David Boyd Melvin, Loveland, OH (US); Alan J. Melvin, Cincinnati, OH (US); Brad A. Klosterman, Nashville, TN (US)

(73) Assignees: University of Cincinnati, Cincinnati, OH (US); CardioEnergetics, Inc., Cincinnati, OH (US)

( * ) Notice: Subject to any disclaimer, the term of this patent is extended or adjusted under 35 U.S.C. 154(b) by 0 days.

(21) Appl. No.: 09/975,214

(22) Filed: Oct. 11, 2001

(65) Prior Publication Data

US 2003/0073912 A1 Apr. 17, 2003

(51) Int. Cl.[7] .................................................. A61B 5/02
(52) U.S. Cl. ........................ 600/508; 600/300; 600/481; 435/284.1
(58) Field of Search ................................ 600/300–301, 600/481, 485, 508, 526, 573, 575, 510; 434/262–275; 435/283.1, 284.1, 287.1; 604/4.01–6.16

(56) References Cited

U.S. PATENT DOCUMENTS

| | | | | |
|---|---|---|---|---|
| 5,586,438 A | * | 12/1996 | Fahy | 62/78 |
| 5,716,378 A | * | 2/1998 | Minten | 607/3 |
| 5,786,136 A | * | 7/1998 | Mayer | 435/1.2 |
| 6,100,082 A | * | 8/2000 | Hassanein | 435/284.1 |

FOREIGN PATENT DOCUMENTS

WO    WO 01/91828    12/2001

OTHER PUBLICATIONS

Unknown, *Untitled Report*, Medical Industry Today; dated Oct. 10, 2001; category Devices.

Slater, James P., M.D., Lipsitz, Evan C., M.D. et al., *Use of Explanted Human Hearts as a Model for the Study of Cardiac Pathophysiologic Conditions*, J. Thoracic and Cardiovascular Surgery, Jul. 1995.

* cited by examiner

*Primary Examiner*—Robert L. Nasser
*Assistant Examiner*—Patricia Mallari
(74) *Attorney, Agent, or Firm*—Wood, Herron & Evans, LLP (57) ABSTRACT

A system for studying a beating explanted heart comprises a fluid inflow circuit configured for coupling to an explanted heart to direct fluid for flowing into a ventricle of the heart, and a fluid outflow circuit configured for coupling to an explanted heart to direct fluid flowing out of the ventricle of the beating heart. A flow meter coupled with the inflow circuit measures the inflow rate of fluid into the heart ventricle and a flow meter coupled with the outflow circuit measures the outflow rate of fluid out of the heart ventricle. A processing system converts the inflow and outflow rates into incremental volume changes in the volume of the heart ventricle and adds and subtracts the incremental volume changes from a relative volume of the heart ventricle to study volume changes in the explanted heart while it is beating.

37 Claims, 5 Drawing Sheets

SYSTEM FOR STUDY OF GLOBAL UNI-OR BI-VENTRICULAR FUNCTION OF AN EXPLANTED, REPERFUSED HEART

FIELD OF THE INVENTION

This invention relates generally to studying the natural heart in operation and, more specifically, to a system for doing so with the heart explanted outside of the body.

BACKGROUND OF THE INVENTION

The natural human heart and accompanying circulatory system are critical components of the human body and systematically provide the needed nutrients and oxygen for the body. As such, the proper operation of the circulatory system, and particularly, the proper operation of the heart, are critical in the overall health and well-being of a person. A physical ailment or condition which compromises the normal and healthy operation of the heart can therefore be particularly critical and may result in a condition which must be medically remedied.

Specifically, the natural heart, or rather the cardiac tissue of the heart, can fail for various reasons to a point where the heart can no longer provide sufficient circulation of blood for the body so that life can be maintained. To address the problem of a failing natural heart, solutions are offered to provide ways in which circulation of blood might be maintained and improved.

Some solutions involve replacing the heart. Other solutions are directed to maintaining operation of the existing heart. One such replacement solution has been to replace the existing natural heart in a patient with an artificial heart or a ventricular assist device. However, such devices have drawbacks which limit their use to applications having too brief of a time period to provide a real lasting benefit to the patient.

An alternative procedure also involves replacement of the heart and includes a transplant of a heart from another human or animal into the patient. Such a technique also has certain drawbacks. For example, the number of potential donor hearts is far less than the number of patients in need of a natural heart transplant. In addition to requiring removal of an existing organ (i.e. the natural heart) from the patient for substitution with another organ (i.e. another natural heart) from another human, the substitute organ must be "matched" to the recipient, which is difficult, time consuming, and expensive. Furthermore, a risk continues to exist that the recipient's body will still reject the transplanted organ and attack it as a foreign object.

Other attempts to assist the heart, such as wrapping skeletal muscle tissue around the natural heart for contraction, or using an external bypass system, such as a cardiopulmonary (heart-lung) machine, are also accompanied by certain problems or drawbacks. Enveloping a substantial portion of the natural heart with a pumping device for rhythmic compression has also been an attempt to address heart failure. Such attempts and other solutions are set forth in greater detail in U.S. patent application Ser. No. 09/850,554, filed May 7, 2001, entitled "Heart Wall Actuation Device for the Natural Heart," which is incorporated herein by reference in its entirety.

Another solution, mechanical ventricular wall actuation, has shown promise. As such, devices have been invented for mechanically assisting the pumping function of the heart, and specifically for externally actuating a heart wall, such as a ventricular wall, to assist in such pumping functions.

Specifically, U.S. Pat. No. 5,957,977, issued Sep. 28, 1999, entitled "Activation Device for the Natural Heart Including Internal and External Support Structures," which is incorporated herein by reference in its entirety, discloses an actuation device for the natural heart utilizing internal and external support structures. U.S. patent application Ser. No. 09/850,554, also discloses actuation devices.

For determining the long-term efficacy of such actuation systems, their operation around and on the heart must be determined. While testing on live animals, and possibly humans, might be desirable, testing on hearts studied out of the body, or ex vivo, is often more practical and desirable. It has been known since the late 19th century that a heart may be isolated ex vivo as a model for the study of myocardial function. This was initially done with animal hearts, requiring the use of animal-derived data to extrapolate to the human condition. Later, human hearts were obtained from cardiac transplant recipients and were restored to a beating condition by being placed on a cardiopulmonary bypass circuit immediately after explantation from the body.

However, existing heart explantation systems have had some limitations and have precluded the study of global functions, including valvular apparatus, as well as the myocardium. For example, one such explanted heart system operates utilizing models which work via balloons placed in one or both of the ventricles. Such balloons totally bypass the valves and rigidly fix the base of the ventricle. In such a system, the volume assessment of the ventricles has been based either on balloon volume or on assumptions, such as conductance or impedance measurements.

Some systems use crystal-based sonomicrometry techniques which are invalid if ventricular shape changes during an intervention. Also, such systems use large numbers of sonocrystals which make the system expensive. Still further, it is time consuming to precisely position and place the large number of sonocrystals.

An additional problem with existing explanted heart systems is that the hearts are generally suspended by their base, which creates an intracavitary gravitational pressure gradient (from base to apex) that, in diastole, approaches or exceeds the physiologic pressure range for the heart.

Accordingly, it is desirable to provide a system for testing an explanted heart which addresses shortcomings of existing systems, and provides useful data regarding the effect of external conditions on the human heart.

More specifically, it is desirable to have a system which is adaptable to either animal hearts or to human hearts removed for transplant, and which allows previously difficult or impossible ex vivo assessments of devices utilized in the treatment of heart failure. Specifically, it is another objective of the invention to provide such an ex vivo system for testing devices which, either statically or dynamically, change or assist the ventricular operation of the heart to address the effects of heart failure.

It is still another objective of the invention to provide such an assessment system for determining the effect of other factors, such as pharmacological compositions, on the human heart within an ex vivo system.

These objectives and other objectives will become more readily apparent from the further description of the invention set forth below.

SUMMARY OF THE INVENTION

The present invention provides a system and method for studying a beating explanted heart. To invention is utilized to study the characteristics of the heart, and to provide ex vivo assessments of external devices and pharmacological compositions on the heart, such as in the treatment of heart failure or heart disease. The present invention provides a system which creates accurate pressure-volume curves and reduces gravitational effects on the explanted heart. The system maintains valvular function in a nearnormal state while the heart is being studied to determine the effect of interventions on the operation of the valves. The system further provides a high-fidelity, high-frequency ventricular volume determination without requiring the expense and placement of a large number of individual sensors.

In one embodiment, a fluid inflow circuit, including an inflow chamber and a compliance chamber, is coupled to an explanted heart to direct fluid for flowing into a ventricle of the heart, such as through the atrium, or directly into the ventricle through a ventricular inflow valve. The fluid outflow circuit is configured to direct fluid flowing out of the ventricle of the beating heart. Respective flowmeters are coupled with the inflow circuit and the outflow circuit for measuring the inflow rate of fluid directed into the heart ventricle, and out of the heart ventricle. A pressure sensor is coupled to the ventricle being tested, which may be the right ventricle, left ventricle, or both ventricles, for measuring ventricular pressure in the ventricle. A processing system receives the inputs from the respective flowmeters and the pressure sensor for graphing pressure changes vs. volume changes and generating curves which are indicative of the performance of the heart. The flowmeters provide varying flow rates over time which are converted into incremental volume changes over time in the volume of the heart by the processing system. The incremental volume changes are then added and/or subtracted from a relative volume of the heart ventricle. A baseline volume determination may be made or proximated by echocardiographic images utilizing geometric assumptions or Simpson's Rule, for example. One suitable inflow circuit comprises an inflow chamber wherein the pressure of the inflow fluid may be selectively varied. In one embodiment, the inflow chamber might be coupled to an overflow device which is vertically adjustable with respect to a level of fluid in the inflow chamber for varying the pressure in the chamber and thereby vary the pressure on the fluid flowing into the heart. Alternatively, or simultaneously, the inflow chamber might be coupled to a compliance chamber which creates a variable pressure in the inflow chamber. A resistor, or throttle valve, is coupled between the inflow chamber and the overflow device for regulating the effect of the overflow device on the fluid pressure of the inflow chamber.

An outflow circuit comprises an outflow chamber for collecting fluid flowing out of the heart ventricle wherein the pressure of the outflow chamber is selectively adjustable for varying the pressure of fluid flowing out of the heart ventricle. The outflow circuit may comprise a compliance chamber coupled to the outflow chamber which creates the variable pressure. One embodiment of an outflow compliance chamber includes a flexible diaphragm positioned in the outflow chamber for interfacing with the fluid in the outflow chamber and preventing a direct air-fluid interface in the outflow chamber, such as to prevent frothing of blood pumped through the system. Pressure sensors coupled in the inflow and outflow chambers provide measurements of the pressures therein.

A collection apparatus is positioned with respect to the explanted heart for capturing fluid which may leak from the beating explanted heart. The collection apparatus is coupled in line with the inflow circuit to deliver the captured fluid to the inflow chamber for ultimate delivery into a ventricle of the heart. To that end, a heart/lung machine might be coupled between the collection apparatus for oxygenating and treating the fluid, such as blood, which is flowing in the system, and delivering it to the inflow chamber. The heart/lung machine will include appropriate pumps for delivering fluid to the inflow chamber. A dialysis circuit might also be coupled for further treating the blood or other fluid pumping through the explanted heart. Oxygenated blood is also provided to coronary vessels of the explanted heart by a suitable sub-circuit.

Fluid received by the outflow chamber might be directed back into the collection apparatus for being pumped back into the inflow chamber, such as through the heart/lung machine. Alternatively, the output of the outflow chamber might be directed back into the inflow chamber. The outlet tube or line from the outflow chamber includes a resistor or throttle valve for adjusting the resistance to flow out of the outflow chamber.

In accordance with one embodiment of the present invention, the collection apparatus, which is configured for capturing fluid which may leak from the beating explanted heart, comprises a flexible bag or sack which is configured to surround the heart and collect leaking fluid. The bag or sack is suspended or floated within a bath of fluid, which surrounds the bag and provides an outer pressure on the bag and the explanted heart therein, to counteract any fluid pressure inside of the heart. In that way, gravitational effects of fluid within the suspended, explanted heart, are reduced. The flexible bag includes an outlet for draining fluid which may include a rigid tube to prevent blockage of the outlet and enhance the draining of fluid, such as into a heart/lung machine to be delivered back to the inflow chamber. Alternatively, a rigid collection apparatus, such as a sink device.

The processing system of the invention receives inputs from the various sensors and meters, such as the flowmeters, ventricular pressure sensor, and the fluid pressure sensors in the inflow and outflow chambers, and processes the data to provide desirable pressure-volume curves. Other inputs from the heart, such as ECG/EKG inputs and average flow rates, might also be utilized by the processing system.

In one embodiment of the invention, the system is configured for testing one side of the heart, such as the left or right side of the heart. However, the inventive system is also applicable to testing the entire heart, and essentially the components for one side of the heart are duplicated significantly for the other side of the heart, although some components are commonly used for both sides of the heart.

These features, and other features of the invention are discussed further hereinbelow in the Detailed Description of the Invention.

BRIEF DESCRIPTION OF THE DRAWINGS

The accompanying drawings, which are incorporated in and constitute a part of this specification, illustrate embodiments of the invention and, together with a general description of the invention given below, serve to explain the principles of the invention.

DETAILED DESCRIPTION OF THE EMBODIMENTS

The present invention is a system for assessing functions of an explanted heart, or part of a heart, that has been excised, reperfused and restored to beating, working condition. In describing these systems, the system components will be set forth for single systems for assessing one side of the heart and which may be the left ventricle with or without the left atrium, or the right ventricle with or without the right atrium. Then, the connections necessary for combining components of two such single systems into a dual system for assessing the entire heart function are described.

Figure 1:
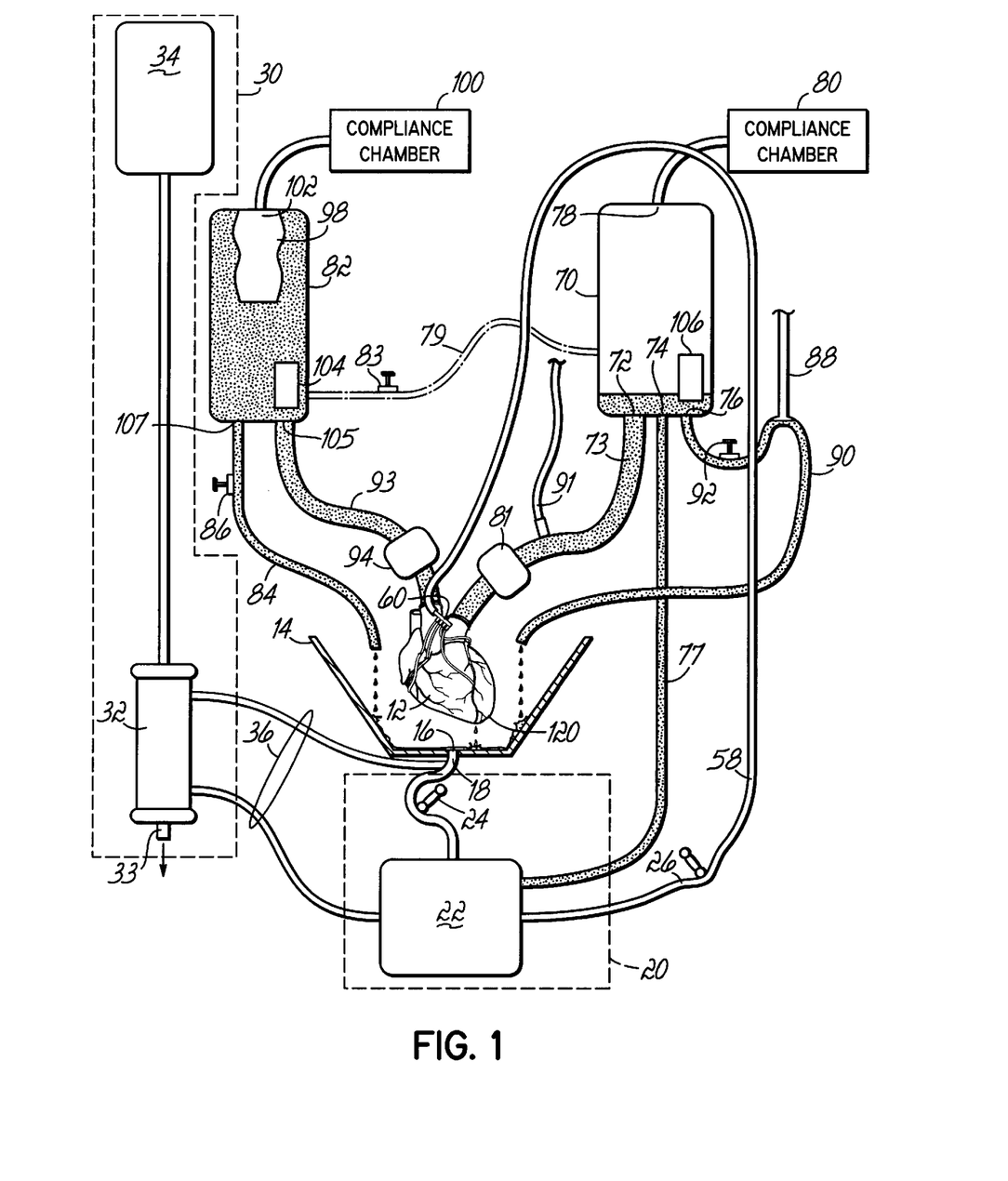
FIG. 1 is a schematic diagram of a system for studying an explanted heart in accordance with principles of the present invention.
Figure 2:
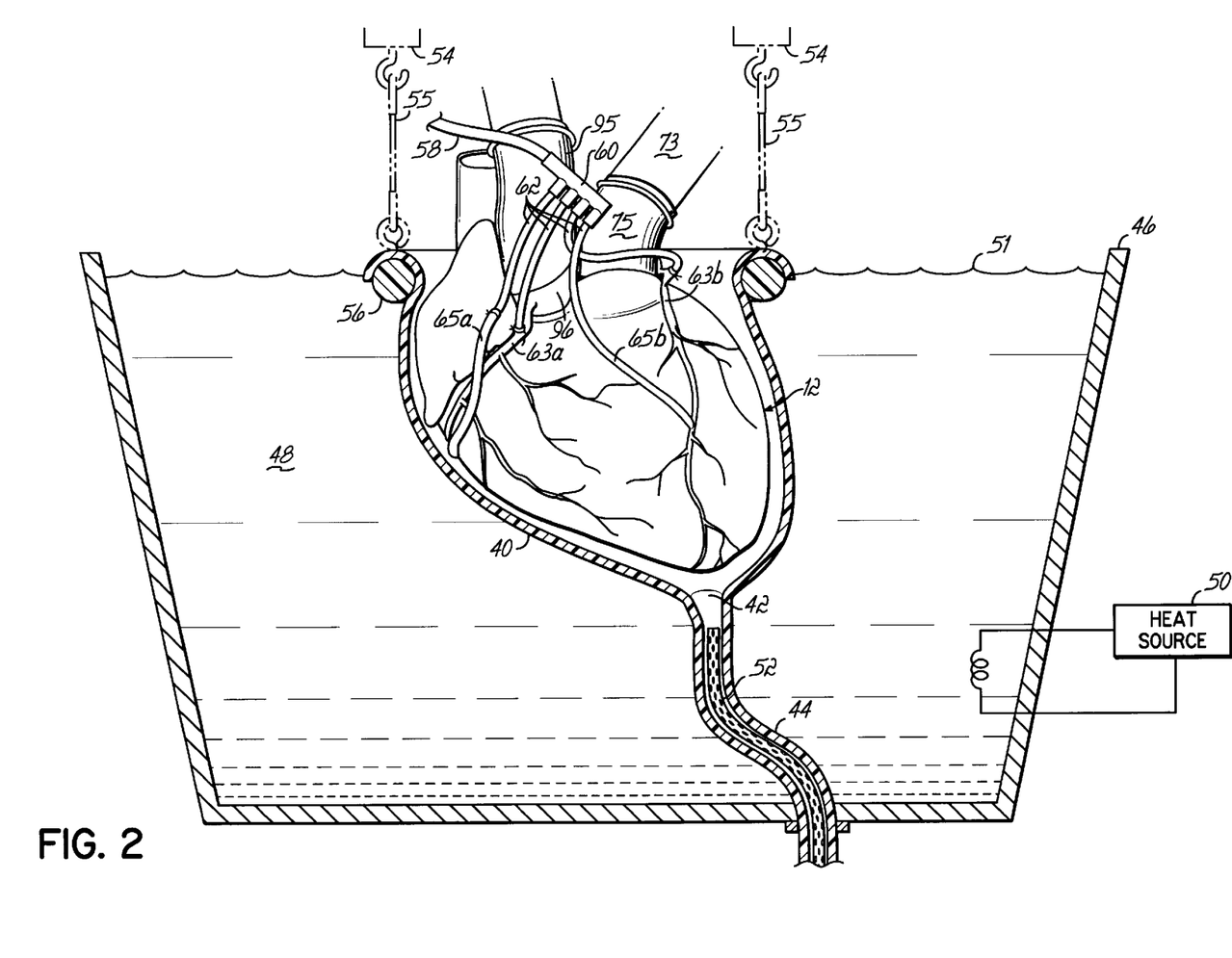
FIG. 2 is a perspective view of an explanted heart showing connections made as part of the inventive system and illustrating a support system for the explanted heart during testing.

The system 10 is shown in FIG. 1 with an explanted heart 12 attached thereto. Herein, portions of the system 10 are referred to as "circuits," such as inflow circuits and outflow circuits, each having various components. The circuits ensure that the perfused fluid, such as blood, is delivered into and pumped out of the heart or delivered to the coronary vessels for feeding the heart and keeping it alive during its study. FIG. 2 also shows the connections made to one side of the explanted heart, primarily the left side of the heart as described further hereinbelow to incorporate the explanted heart into the invention.

System 10 and its circuits and various subsystems will generally be coupled to a support framework (not shown) for supporting various of the components of the system. Such a framework might be stationary or may be coupled to a moveable apparatus, such as a cart (not shown).

In accordance with one aspect of the present invention, the explanted heart is suspended above or surrounded by a collection apparatus for collecting blood or other fluid which may leak from the explanted heart, such as from around the points where the explanted heart connects to the system 10. The leaked blood or fluid is then captured and brought back into the system as described further hereinbelow. One such collection apparatus is illustrated in FIG. 1 and includes a generally rigid funnel or basin 14 which collects blood from the explanted heart or from overflow from various of the system chambers. The funnel 14 includes an outlet 16 which is coupled by line 18 to a heart/lung subsystem 20 for oxygenating and otherwise treating the blood and pumping the blood or other perfusate for use within the overall system 10.

The heart/lung subsystem 20 includes an oxygenator 22, which may be a commercially available piece of equipment known to those skilled in the art, and a first pump 24 for pumping the blood through the oxygenator and the overall system 10. A second pump 26 is used to perfuse the coronary circulation with blood. Heart/lung subsystem 20 may also be coupled with a dialysis circuit 30. The subsystems 20 and 30 might be a collection of components which are used clinically for "open heart" operations or might be custom assembled components. The pumps 24, 26 may be centrifugal pumps or other suitable pumps. Oxygenator 22 might be a membrane oxygenator.

The dialysis subsystem 30 includes a dialysis cartridge 32 with a reservoir of dialysate fluid 34. The associated tubing loop 36 circulates the fluid between circuit 30 and subsystem 20. Cartridge 32 may include a port 33 for disclosing fluid that has circulated through the cartridge.

FIG. 2 illustrates an alternative embodiment of a collection apparatus to surround the heart and collect blood within the system. Referring to FIG. 2, a flexible bag or sack 40 is formed and positioned to surround the heart 12. The collection bag 40 collects blood which leaks from the heart, and also collects other blood from the system 10 as discussed further hereinbelow. Collection bag 40 includes a drainage outlet 42 and associated drainage tube 44 which, referring to FIG. 1, would feed into the oxygenator 22. The collection bag 40 is suspended or supported within a tub 46 filled with a fluid 48, such as water, so that a bath of fluid surrounds the bag and heart. So that the heart 12 is not unnaturally chilled, which may affect its function, the fluid 48 is heated, such as by a heater system 50 coupled to tub 46 and the fluid therein. Drainage tube 44 passes through an appropriate outlet port in the tub for coupling to oxygenator 22. The collection bag 40, in one embodiment, incorporates a perforated tube 52, generally coaxial with tube 44, which has suitable rigidity to ensure that drainage is maintained through the collection bag 40 without the heart blocking the outlet 42 while having the tube 44 otherwise be compressed to hinder flow of blood therethrough. In that way, the outward flow of blood from the collection bag 40 is not obstructed.

Bag 40 is not liquid permeable. Therefore, the collected blood is isolate from the water or other fluid 48 within tub 46. In addition to the collection of blood, the collection bag 40 also provides desirable support of the heart 12 within the system 10. This provides a significant benefit over other explanted heart systems by reducing and avoiding gravitational gradients in pressure within a suspended heart.

For example, should the heart be supported to hang from components of the circulation system, gravitational effects create gravitational grading and some pressure across the walls of the heart. In accordance with this aspect of the present invention, by suspending the heart within the flexible collection bag positioned within the tub of fluid, constant transmural pressure is achieved because at each vertical distance increment both in the heart within bag 40 and in the bath or tub of fluid 48 outside of the bag, an equal pressure increment is added or subtracted in the heart wall due to the height of fluid above that point. To that end, it is generally desirable to have as much of the heart as is practical below the upper level 51 of the liquid 48. The collection bag is in the form of a suitable, waterproof and flexible material, such as polyvinyl chloride, polyethylene, or polyurethane. This aspect of the invention negates the variation in pressure differences across the walls of the heart that are attributable to the height differences in a suspended heart. In doing so, the invention eliminates the "teardrop" deformity which sometimes occurs in a relaxed suspended ventricles and restores the forces and shape of the heart and ventricles to near those observed within the intact living body.

The fluid 48 may be water or other fluid which has a negligible difference in density from the heart-perfusion fluid which may generally be blood. Referring again to FIG. 2, the collection bag 40 may be supported directly from the framework 54 and suitable tethers 55 or other structures coupled to the collection bag 40 around its periphery. As noted, the suspension desired would maintain as much of the heart as possible below the level 51 of fluid 48, without allowing the fluid 48 to fill into the bag and mix with the blood. In an alternative embodiment, also illustrated in FIG. 2, a floatation device 56, such as a floatation ring, may be coupled to the periphery of the collection bag 40 surrounding the opening which receives the heart and thereby floats or supports the top of the bag above level 51 of the fluid 48.

Therefore, the present invention provides physiologic accuracy by negating the gravitational gradings and pressure which may occur within a suspended heart filled with fluid which is simply hanging or is suspended in mid-air. This also better allows fluid to be pumped through the heart, by the heart, and allows the elimination of balloons as used with prior systems. This arrangement results in a more accurate study of the beating heart.

Referring again to FIG. 1, as is illustrated by tube 58, the heart/lung subsystem 20 is coupled to coronary trunks or vessels of the heart for supplying the heart with blood and maintaining the heart muscle during any testing or use of the system 10, so that the beating heart is kept alive. Referring to FIG. 2, tube 58 is coupled to a manifold 60 with associated coronary cannulae 62 which extends into both main coronary trunks or vessels 63a, 63b and/or into any arterial or venous coronary bypass grafts 65a, 65b which have sufficient lumen for cannulation. In that way, blood flow is delivered to the beating heart muscle for proper physiologic operation during testing of the heart. System 10 includes an inflow subsystem or circuit, and an outflow subsystem which will be described herein separately for a single side of the heart, such as the left side of the heart, for measuring the physiologic characteristics of the left ventricle and general left side of the heart. In a system for testing the entire heart, such inflow and outflow subsystems will essentially be duplicated, although not entirely, for the right side of the heart (see FIG. 6).

Referring again to FIG. 1, the inflow subsystem or circuit comprises an inflow chamber 70 having multiple input and output ports for passage of fluid, such as liquid or gas, therethrough. The inflow chamber 70 is mounted on the support structure (not shown) which supports other components of system 10. In the embodiment of the system illustrated in FIG. 1, the input chamber 70 is shown to have three bottom ports 72, 74 and 76 and one top port 78. The top port 78 may be coupled to an optional compliance chamber 80 which may be utilized so that the inflow system more closely mimics the physiology of the heart associated with the inflow of fluid into the heart. Generally, an inflow compliance chamber 80 will be utilized when the overflow circuit of the inflow subsystem 70 is disable as discussed further hereinbelow. Luer lock ports may be added to the inflow chamber 70 or to the associated ports 72, 78 as necessary for pressure sensing, sampling and/or infusions.

Inflow chamber 70 is coupled through port 72 to tube 73 and ultimately into one side of the heart through a flow meter 81. The fluid flow tubes, such as tube 73, utilized throughout the system are preferably compliant, surgical grade tubes which provide the necessary characteristics for the flow of blood or other perfused fluid within the system. Various materials suited for such purposes are known to one skilled in the art. The tube 73 or inflow connector which connects the inflow chamber 70 to heart 12 has an end which is a surgical grade material which may be either sown to the fibrous annulus of ventricular inflow valve (mitral or tricuspid) or attached to an opening in the atrium of the side of the heart being studied, such as by being sown to a flexible connector or tied to a rigid connector. The inflow circuit directs fluid for flowing into the heart ventricle and therefore may direct the fluid into an atrium first, or directly into the ventricle through an inflow valve (e.g. mitral or tricuspid). Such connections can be made on either the left or right side of the heart, depending on the testing scenario.

Referring now to FIG. 2, tube 73 is shown with the connection end 75 coupled into the left atrium proximate the mitral valve. The cannulae are shown going into the left and right main coronary arteries at their origin after detachment from the aortic route. They are also shown passing into two bypass grafts including an internal thoracic arterial intravenous conduit. Aortocoronary "stumps" have been oversewn or ligated.

The inflow chamber 70 is adjustably coupled to the framework supporting the system 10 so that the vertical height of the inflow chamber 70 may be adjusted independently of the height of the heart. This allows for a gross adjustment of the heart inflow pressure of the system presented through the tube 73. Inflow chamber 70 collects blood from the oxygenator via port 74 and tube 77. Alternatively, or in addition to blood from the heart-lung subsystem 20, the inflow chamber may collect blood via tubing 79 from an outflow chamber 82 which includes a suitable throttle valve or outflow resistor 83. As illustrated in FIG. 1, outflow blood from chamber 82 might drain directly into the collection apparatus 14 or collection bag 40 through an appropriate tube 84 and outflow throttle valve or resistor 86. While varying the height of the inflow chamber provides gross adjustment of the heart inflow pressure, an overflow tube is utilized for fine adjustment of the heart inflow pressure. The overflow tube is also adjustably coupled to the structure supporting the components of the system 10 so that its height may be vertically adjusted both with respect to heart 12 and also with respect to the inflow chamber 70. Flexible and adjustable tubing 90 couples the overflow tube 88 to the inflow chamber 70 and allows the overflow to drain into a collection apparatus 14, such as collection bag 40.

The positioning of the inflow chamber relative to the ventricle within heart 12 dictates the range of vertical distance that the overflow tube 88 may be adjusted between the inflow chamber blood level and mid-ventricle. The overflow tube 88 altitude actually determines the blood level inside the inflow chamber 70 and thus its vertical height above, or conceivably below, any given point, for example the vertical midpoint within the ventricle. Varying the height of tube 88 with respect to chamber 70 allows fine adjustment of the inflow pressure and through the flow meter 81. As such, gravity is used to provide adjustment of the pressure. To remove the effects of the overflow tube 88 from the pressure variance of the inflow chamber 70, a throttle valve 92 may be utilized in the connector tube between the overflow tube 88 and chamber 70. By removing the overflow tube 88 from the circuit, a compliance chamber 80 might be utilized instead to provide a more accurate physiological adjustment to the inflow pressure. Alternatively, a segment of smaller caliber tubing might be utilized to reduce the effects of the overflow tube in addition to, or rather than, the throttle valve 92 which may be utilized to constrict or dampen the outflow. In another alternative embodiment, a one-way (outwardly directed) valve may be employed. This allows the overflow level to be set at the maximum phasic pressure to be reached in the inflow chamber during the cardiac cycle, while the filling behavior of the ventricle and rate of blood return from the outflow chamber determine phasic atrial pressure.

The compliance chambers utilized with the various flow chambers, such as inflow compliance chamber 80 are used to control the time variation of the pressure (dp/dt) in the blood chambers. Without sufficient compliance, blood chamber pressures would transiently increase and decrease excessively as heart valves opened and closed. In one embodiment of the invention, each compliance chamber is a large, adjustable-volume air container which have walls which are not themselves appreciably compliant. Compliance is controlled by an air-volume adjustment, such as by offsetting less or more of the total volume in the chamber with water. The inflow compliance chamber will connect with an air space above and in contact with blood in the chamber.

The adjustable-volume inflow compliance chamber 80 utilizes a variable air-space mechanism or other mechanism to alter its own, and therefore the inflow chamber's pressure/volume relationship. The connections and connector bores from the blood of the various inflow or outflow chambers to the associated compliance chambers are large (for example, greater than 3/8 inch) to facilitate equilibration. Air volume in the inflow compliance chamber is much greater than that in the outflow compliance chamber. This follows the physiologically greater compliance (lesser pressure change in response to a given volume change) in venous than in arterial circulations.

In another alternative embodiment, such as for studies where faithful replication of venous compliance is not critical, port 78 to the inflow compliance chamber may be open to the atmosphere, providing infinite compliance.

A cannula 91 is coupled with outflow tube 73 for addressing an undesirable pressure buildup within the ventricle. Before the explanted heart begins to pump within the testing system, the cannula, which is perforated, is positioned across the valve, such as in a transmitral position, to provide decompression. Once the heart begins to beat and pump, the perforated cannula can be withdrawn as discussed further hereinbelow regarding the operation of the system. Any blood from cannula 91 may be directed back into the system such as into the collection apparatus or into the inflow or outflow chambers.

Turning now to the outflow side or circuit of the system, outflow chamber 82 is coupled to a ventricle of heart 12 through tube 93 and flow meter 94. Tube 93 is coupled to the heart 12 by tying on or sewing a supra-annular connector 95 (as seen in FIG. 2) to a portion of the aorta 96 for the left side of the heart, or a portion of the pulmonary artery on the right side of the heart. The outflow connector 95 may be configured either for sewing to the annulus of the outflow valve, which is the aortic or pulmonic valve at the side of the heart. Alternatively, the outflow connector may be configured for ligation-fixing to the outflow vessel, such as the aorta or pulmonary artery as noted above.

The outflow chamber 82 may resemble the inflow chamber 70. However, it may be preferable to prevent an air-blood contact in chamber 82 to avoid frothing and foaming of the blood in the outflow chamber. Flow of blood into the outflow chamber 82 may be vigorous due to the vigorous ejection of blood from the ventricle. To prevent direct air-blood contact and to avoid foaming, outflow chamber 82 may incorporate a polymer-membrane diaphragm or immersed "sock" 98. The diaphragm 98 is coupled to an outflow compliance chamber 100 to provide pressure equilibration without air-blood contact. Compliance chamber 100 will generally have the same effective purpose of compliance chamber 80 described above with respect to the inflow chamber to provide control of any excessive increases or decreases in pressure versus time as the heart valves open and close. While the diaphragm 98 might also be used in the inflow chamber, the lesser turbulence in the inflow appears to obviate the need for such a diaphragm.

The outflow chamber includes various input and output ports. One output port at the top of the chamber is port 102 which provides coupling between diaphragm 98 and the compliance chamber 100. An input port 105 is provided for coupling outflow tube 92 to the chamber 82. An output port 107 couples to tube 86 which drains blood from the outflow chamber. In one embodiment, the fluid may be directed back into the collection apparatus 14 as illustrated in FIG. 1. Alternatively, a suitable port or connection might be provided to couple to tube 79 to direct outflow blood or fluid directly back into the inflow chamber 70 rather than have it pass through the heart/lung subsystem. Therefore, the outflow chamber may feed into the inflow chamber. Suitable throttle or resistor valves 83, 86 may be utilized for controlling the outflow pressure. While outflow chamber 82 is shown with flexible diaphragm 98, the diaphragm might be eliminated for simpler construction in exchange for possible foaming of the blood. Throttle valves 83, 86 may be similar to the valve 92 and may be a tube-compressing throttle, gate valve, or another resistance mechanism having a similar effect to adjust the resistance of fluid flow out of the outflow chamber 82.

Components described with respect to system 10 provide for a pumping operation of an explanted heart and a profusion of blood through the heart for more realistic testing and evaluation of the heart's function. In addition to the physical structures for providing pumping of the heart, system 10 also utilizes an assembly of sensors and data acquisition hardware and software to monitor cardiac function. The assembly provides a continuous record of pressure and relative volume in one or both ventricles of the heart being studied. Those records may then be used to record and display pressure-volume relationships and indices of ventricular function, such as end systolic pressure-volume relationship or $E_{max}$, based on those relationships. Pressure is derived from an intraventricular pressure sensor. Further volume is computed by integration of the flow signals from the inflow and outflow flowmeters or flow sensors, 81, 94. Those flow meter readings are then added and subtracted respectively from the relative volume at a relatively high frequency which is generally greater than 1 KHz. Absolute volume is approximated by echocardiographic images in two planes of the ventricular wall being. Either end systolic or end diastolic (for the fullest or emptiest portion of the cardiac cycle) volume of the ventricles is computed either by geometric assumptions or by Simpson's Rule and used to calibrate that portion of the continuing relative volume curve.

Referring again to FIG. 1, an outflow pressure sensor 104 is positioned within the outflow chamber 82 wherein an inflow pressure sensor 106 is positioned within inflow chamber 70. The pressure sensors 104, 106 inside the inflow and outflow chambers are suitable sensors, such as fluid filled sensors connected to a remote transducer. The sensors 104, 106 provide a measurement of the inflow and outflow pressures created within the chambers 82 and 70, respectively. The flow meters or flow sensors 81, 94 are coupled in continuity with inflow and outflow tubing and connectors to be coupled into the flow of fluid to and from the heart for measuring that flow. In one embodiment of the invention, the flow meters 81, 94 are ultrasonic. However, they may be electromagnetic or include any other adequately accurate flow sensing system commercially available. The flow meters.81, 94 provide a reading of the amount of fluid flow into and out of the side of the heart to which they are coupled. Flow meter 81 records the flow of fluid which is delivered through the annular sewn-on connector 75 as illustrated in FIG. 2, which might be a mitral connector. Flow meter 94 monitors and records the flow of fluid delivered through the aortic connector 95 coupled to aorta 96. The throttle valves 86, 92 which are utilized for pressure control of the respective inflow and outflow chambers to provide the desired adjustment of the pressures within the system. For example, the throttle valve 86 in the main arterial outflow tube 84 may be used to provide adjustment resolutions for relatively fine control of the outflow of blood within defined pressure gradients. For example, the throttle valve 86 may provide control from zero to ten liters per minute of outflow at pressure gradients varying from 60–200 mm of Hg. Throttle valve 92 is utilized to enable or disable the inflow chamber overflow pressure control. Specifically, the overflow tube 88 provides a pressure control for the inflow chamber and in one embodiment is a height-adjustable open inverted-T connector. During pure gravity-controlled filling pressure operations, it serves as an atmospheric vent and an overflow passage. By setting the height of the overflow tube 88, the inflow pressure is adjusted. For more precise mimicking of normal flow physiology, the throttle valve 92 may be completely closed or very nearly completely closed so that filling pressure is controlled directly by pump flow rate of the pump 24 and by ventricular compliance, with time-variation and pressure controlled by the inflow compliance chamber 80. Again, pump 24 drives the blood flow for ventricular loading at the inflow chamber 70 while pump 26 drives coronary perfusion flow for supplying the heart muscle. The oxygenator structure 22 of the heart/lung subsystem may be a commercially available unit with a gas exchange capacity at least in the range used for 20–30 kg children clinically (or larger, as available).

Figure 3:
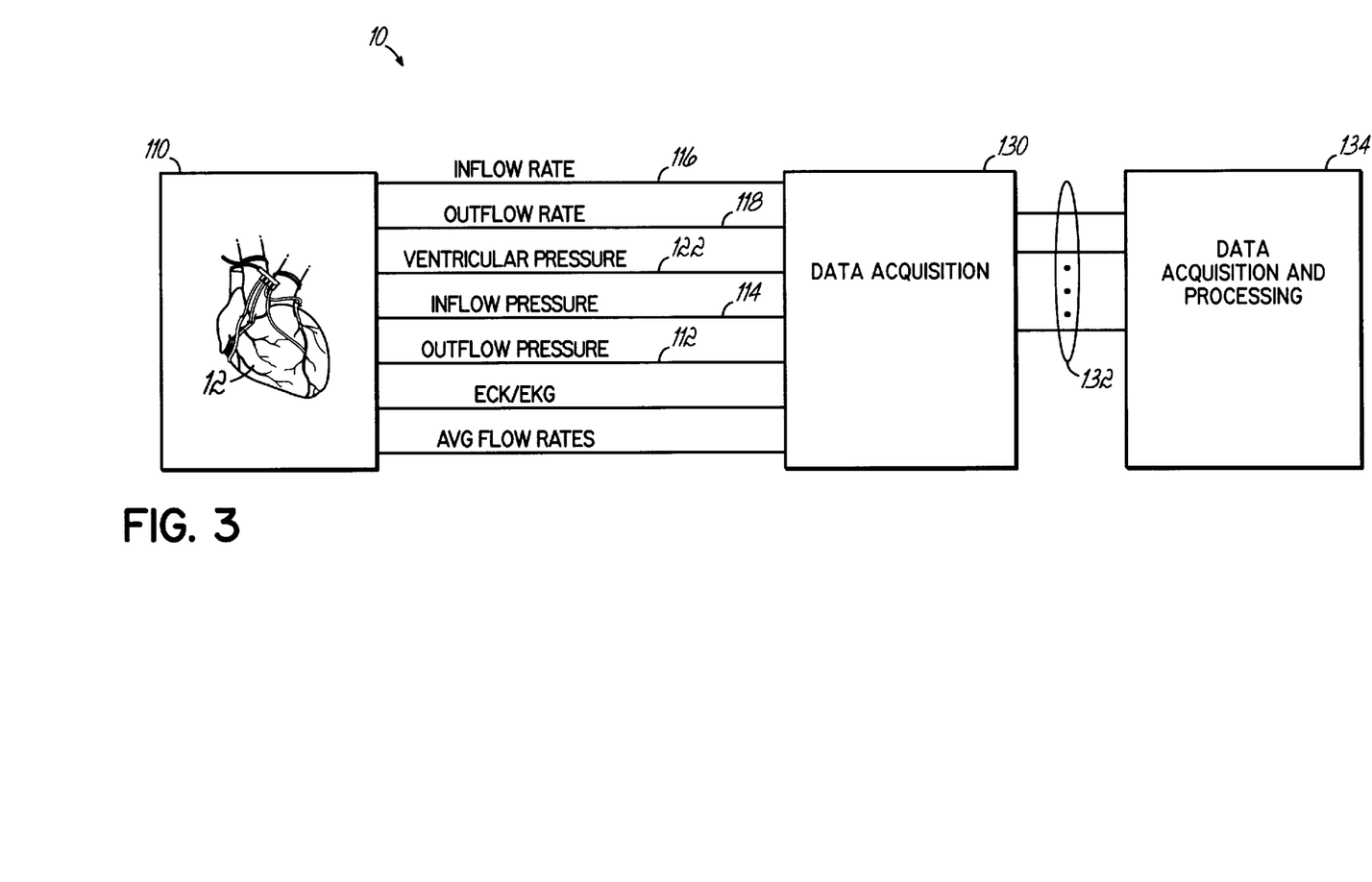
FIG. 3 is a schematic diagram of the sensor and data acquisition components of the inventive system.

FIG. 3 illustrates the sensor and data acquisition and processing system in accordance with one aspect of the present invention.

The plurality of outputs are provided by the beating heart 12 and the system maintaining the beating of the explanted heart, indicated generally by reference numeral 110 within FIG. 3. Pressure sensor 104 within the outflow chamber 82 provides an outflow pressure 112, while pressure sensor 106 within the inflow chamber 70 provides an inflow pressure 114. Such data provided by the inflow and outflow pressure sensors 106, 104 may be utilized to more precisely adjust the pressures within the beating heart, to more accurately portray the physiological scenario of the heart within its natural operation.

Flow meter 81 provides an inflow rate 116, while flow meter 94 provides an outflow rate 118. A precise and solid state pressure sensor 120 is positioned within the heart ventricle being measured, such as inside the left ventricle in the example described herein. The pressure sensor 120 may be, for example, a solid-state, catheter-tip transducer to determine the pressure. Generally, the sensor will be positioned within the ventricle such that it is at the mid-ventricular level. As discussed further hereinbelow, the pressure transducer may be positioned in the ventricle via the ventricular apex. The output of the ventricular pressure transducer is indicated at signal 122 in FIG. 3. The inventive system 10 also includes data acquisition hardware and data signal processing and conditioning hardware and software, and devices such as amplifiers, filters and other electronic conditioning hardware utilized to process raw signals received from the sensors as is understood by a person of ordinary skill in the art and discussed further below. For example, the data acquisition hardware subsystem 130 may include appropriate analog/digital converters for providing digital data which may be readily processed. The hardware 130 may also provide activating signals for any sensors which require such signals, such as electromagnetic flow sensors, if utilized. Such hardware 130 might be assembled from commercially available components, depending upon the various types of sensors which might be utilized and also depending upon the form of the data which is acquired and processed. Data acquisition hardware 130 provides output data on lines 132 to data acquisition and processing hardware and software 134. The present invention acquires raw analog data, converts the data to a digital signal, and provides for real time data analysis as well as storing selected data for post-experiment analysis. One suitable software package utilized for an embodiment of the system is the DASYLab software package as discussed further hereinbelow.

The present system 10 is utilized with an explanted heart which is then restored to beating operation for testing. Herein, the preparation of the heart for measurements will be described.

In utilizing the system in accordance with one aspect, a stable beating heart is desired which has a stroke volume of greater than or equal to 40 ml with a left ventricle end diastolic pressure (LVEDP) less than or equal to 20 mmHg and a mean arterial pressure (MAP) greater than or equal to 70 mmHg if such conditions are obtainable with clinical levels of inotropic drugs. If such a system is not obtainable, it is desirable that operation near these targets is achieved with inotropic support.

In initial preparation of the heart, cardioplegia is desired if not already delivered. Then the perfusate is recirculated with blood and has desirable chemical characteristics. For example:

(a) pH 7.32–7.48
(b) $K^+$ 3.4–5.0
(c) $Ca^{++}$ normal range (ionized Ca, if available)
(d) Hct>=25
(e) T 36–38.5 C° If the desired conditions of the perfusate and blood mixture are achieved, the heart can be mounted within the system. In mounting the heart, the supra-annular connector 95 is sewn or tied on to the aorta 96. Connector 75, which may be a mitral connector for testing the left side of the heart, is sewn to the annulus associated with a particular side of the heart. Coronary cannulae from the manifold 60 couple with both native coronary trunks and into any arterial or venous coronary bypass grafts with sufficient lumen for cannulation as illustrated in FIG. 2. The solid state, catheter-tip pressure transducer 120 is then positioned at mid-ventricular level via the ventricular apex.

The non-working heart is then perfused via the coronary cannulae at 100 mmHg from the oxygenator 22. In doing so, the transducer valve decompression cannula 91 is advanced into the ventricle, such as transmitral into the left ventricle. The throttle valves 86 and 92 are open if they are already in position within the system. The gravity pressure and overflow control within the inflow chamber 70 utilizing overflow tube 88 is positioned at a certain height above the atrial-ventricular valve level, for example 6.5 cm above that valve level. The bottom of the inflow chamber 70 is then positioned about 5 cm below the level of the overflow control 88. The overflow tube 88 and its adjustment range as well as the vertical adjustment range of the inflow chamber 70 are configured to provide the desired adjustment of inflow chamber pressure. Via heart/lung subsystem 20, the heart 12 is then filled at a low pressure. The blood is allowed into the inflow chamber 70 until the blood level of both the inflow chamber and the arterial outflow line 93 are at about 6.5 cm above the atrial-ventricular valve level, providing approximately 5 mmHg pressure in the ventricular base. If there are deviations with respect to the blood and perfusate chemical levels set forth above, those values are reestablished.

Next, to begin the beating of the heart, epicardial pacing wires are positioned on the heart in a conventional way and connected to a pulse generator, such as at 80 beats per minute, asynchronous, full voltage. If there is rate competition, additional atrial tissue is excised.

When the heart is beating, troubleshooting may take place. If there is an unequal distribution of perfusion, the position of the cannula connected to the manifold 60 may be adjusted. Also, the heart tissue might be massaged for visible bubbles in the coronaries. If there are chemical aberrancies, which may be checked five minutes into the perfusion, those chemical levels as set forth above may be corrected with additives and then rechecked. For fibrillation conditions, the counter shock of 25 to 50 J may be used as needed. If fibrillation reoccurs, the shock may be repeated and lidocaine at 25 mg may be started into a pump every thirty minutes. If there is inadequate contraction, such as grossly evident severe hypocontractility (in human hearts, relative to pre-excision), an inotropic drug, such as dopamine, may be started at 0.5 mg then 100 mcg per minute, increasing by 100 mcg per minute each 5 minutes needed for producing a grossly visible response.

If the heart is beating properly, the instruments may be connected and made operational. Data acquisition may be checked by examining the values and curves produced by the data from the various sensors. For example, the ventricular pressure sensor 120 may be positioned and repositioned. The inflow and outflow rates, 116 and 118 may be determined and calibrated at a zero mean flow. Fluid-filled pressure transducer 104 in the outflow chamber may be zeroed at mid-ventricle level for a reading consistent with an estimation. The pump flow rate for pump 24 may then be adjusted if needed to produce a pressure of 60–80 mmHg mean pressure. The fluid-filled pressure transducer 106 of the inflow chamber may be zeroed at mid-ventricular level. The system may then be rechecked so that the desirable perfusate and blood chemical levels are achieved, and the levels may be corrected if necessary. It is then desirable to stabilize the system, such as for fifteen minutes.

If the heart visibly appears to be contracting well in an empty, unloaded condition, a transition may be made to a working preparation. The perforated, ventricular decompression cannula 91 is withdrawn until it is above the valve level, such as above the mitral valve level. The outflow throttle valve or resistor 86 is positioned to be fully open. The vertical level of the inflow chamber is gradually raised and the overflow tube 88 is gradually raised as needed to vary the inflow pressure and provide an outflow rate through sensor 94 that reaches 3 L per minute or an LVEDP greater than 30 mmHg. The flow rate of pump 24 is then increased as necessary to maintain at least a trickle of flow through the overflow line 90 as dictated by the level of overflow tube 88 and the level of the inflow chamber 70. In an alternative embodiment, servo or feed-back control systems may be used to adjust blood flow from the pump-oxygenator into the inflow chamber, rather than the overflow system or manual control. Throttle valve 86 is then tightened until the peak left ventricular pressure reaches 80 mmHg or the aortic outflow rate which is measured falls below 1.5 L per minute. If the output is less than 3 L per minute and the LVEDP is less than 30 mmHg, the height of the inflow chamber and the overflow tube are increased incrementally and the measurements are repeated until the desired outflow rate and/or pressure is achieved. If the desired values of 80 mmHg peak pressure and flow 1.5 L per minute are not achieved in the first or subsequent attempts to transition, the circuits should be returned to a non-working circuit with the decompression or venting cannula 91 to be advanced into the ventricle. After five minutes, a repeat attempt may be made to transition. If this repeat attempt fails based upon the above noted criteria, non-working-status should again be resumed and dobutamine may be administered in step doses until there is a visible increase in the force of contraction of the heart 12. Iteratively, repeat attempts may be made at the transition to achieve a working status. Each failure, whether initial or through deterioration, should be accompanied with additional steps of dobutamine and another trial. As noted above, in the working preparation, the inflow chamber 70 and the overflow tube 88 are raised or lowered to vary the preload pressure. Throttle 86 may be adjusted to vary the afterload pressure. The outflow compliance chamber 100 is adjusted to control arterial pulse pressure. In studies where close modeling of filling pressure variation is important, the inflow compliance chamber 80 is connected and the effect of the overflow tube 88 is generally removed from the circuit by adjusting the throttle valve 92.

After a stable working and pumping heart has been achieved, the stability of the system may be observed for 20 to 30 minutes with the venting cannula 91 withdrawn from the ventricle. Throttle valve 92 is open and throttle valve 86 may be varied as needed to maintain peak systolic pressure of 80–100 mmHg. All flows and pressures may then be recorded at intervals, for example for 10 seconds each every 5 minutes.

After measurements are made, pressure-volume curves may be derived as discussed below, using an arbitrary baseline. The system may then be adjusted with repositioning of the various sensors needed for obtaining credible signals. Pump flow may then be reduced to a point of LVEDP 5 mmHg. The system may then be continuously increased to LVEDP 30 mmHg, recording continuous data for the pressure-volume loops and curves. A pause may be made during each 5 mmHg interval (e.g., between 10 and 15 mmHg, between 15 and 20 mmHg, etc.) to record the short axis and 4-chamber view echos of the heart to determine absolute volume by echo-derived volume calculations.

In accordance with one aspect of the present invention, the volume measurements of the heart are made, along with pressure measurements, to provide pressure-volume curves which are indicative of the operational conditions of the heart under varying stress and load conditions. The present invention may be utilized with a number of different testing criteria to determine the effect of different factors on the operation of the heart. In accordance with one aspect of the present invention, the effect of static, heart-shaping structures may be determined. In accordance with another aspect of the present invention, dynamic actuation systems, to work on and actuate the heart, might also be tested. Still further, the inventive system may be utilized for determining the effect of pharmacological composition on the heart. Therefore, the present invention is not limited to heart tests involving any particular or defined factors which might be utilized to influence the operation of the heart.

In one embodiment of the present invention, absolute volume is approximated by echocardiograhic images in two planes of the ventricle while beating. Either the end systolic or end diastolic volume of the ventricle (that is, the fullest or emptiest portions of the cardiac cycle) is computed, such as by geometric assumptions or by Simpson's Rule and used to calibrate a portion of a continuous relative volume curve.

The inventive system provides a continuous record of pressure and relative volume in one or both ventricles of the heart being studied. The is measured pressure and volume data is then utilized to record and display pressure-volume curves and relationships and indices of ventricular function. For example, the end systolic pressure-volume relationship or $E_{max}$ may be determined based upon measured data. The pressure is derived from the intraventricular pressure sensor 120. Relative volume is computed by integration of the measured flow signals 116, 118 from the inflow and outflow flow sensors, 81 and 94, respectively. The integration involves adding and/or subtracting from the relative volume based upon the output of the flow sensors. This integration is done at a relatively high rate, for example above 1 KHz of frequency. The amount of blood flowing into the heart is associated with a volume change in the heart. In that way, the addition and subtraction and overall integration of the measured flow signals and flow rates from the flow sensors 81 and 94 may be utilized to estimate the volume of the heart based upon the integration of those volume changes with respect to an approximated absolute volume. For example, the volume that is flowed into or out of the ventricle through each flow meter or flow sensor 81, 94 within any time increment is determined by the product of the time increment and the measured flow rate within that time increment. If the measured flow is out of the ventricle, the volume is sequentially subtracted from the relative volume (i.e., absolute volume minus any previous volume subtractions plus any additions). If flow is measured into the ventricle, the volume increment is added to the relative volume. This yields a running and frequent computation of relative volume. The relative volume may be corrected to absolute volume by periodically entering echo-derived volume calculations as discussed above.

In one embodiment of the invention, the data may be recorded in a spreadsheet format and reflective curve values determined from the spreadsheet. Alternatively, in another embodiment of the invention, analytical software packages, such as DASYLab™ from DASYTech, Amherst, New Hampshire, and National Instruments Corporation, Austin, Tex., might be used.

Figure 4:
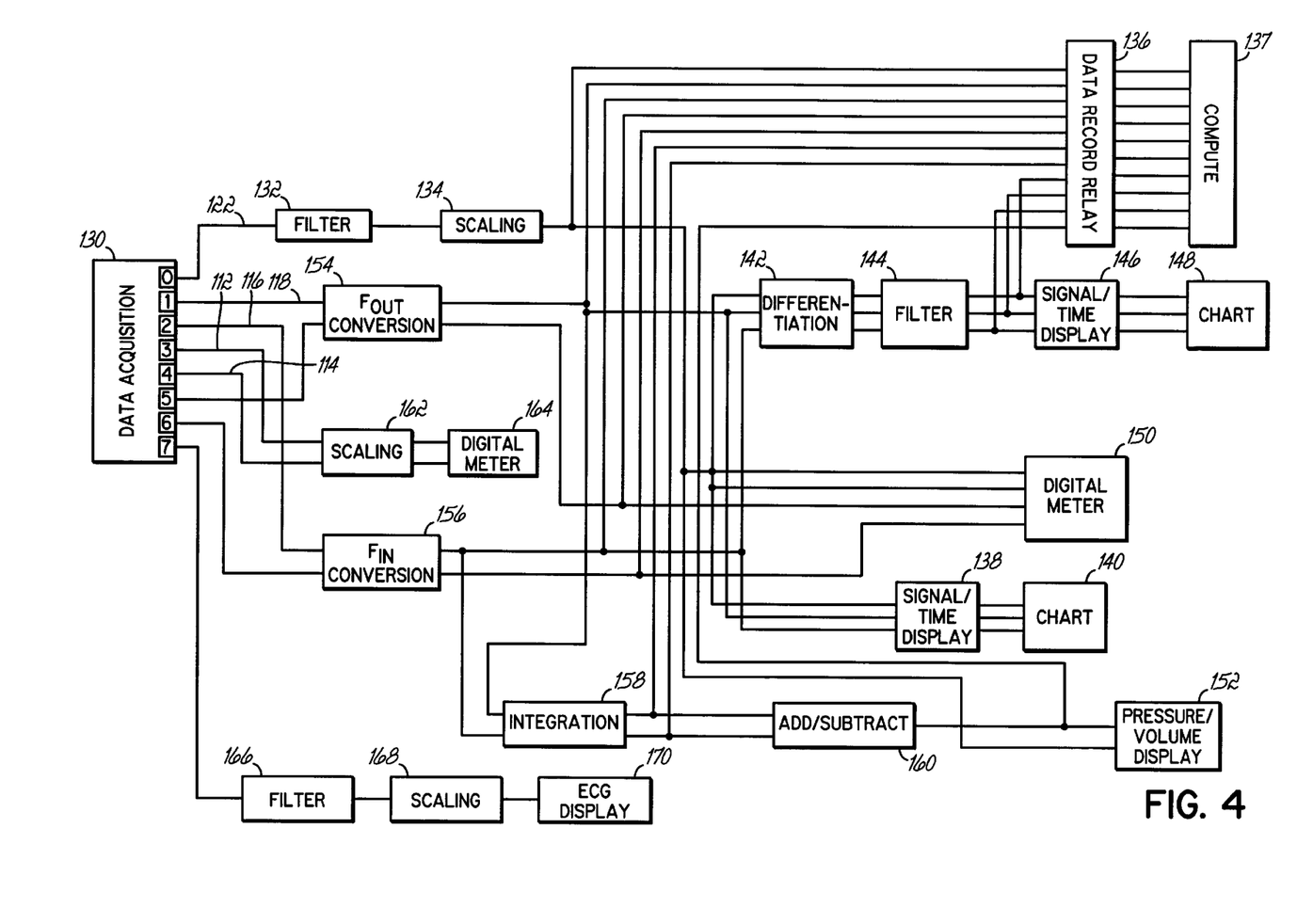
FIG. 4 is a schematic view of a computer worksheet for data processing the sensed signals in one embodiment of the invention.

FIG. 4 illustrates a work sheet from a DASYLab™ software package showing various of the connections and inputs and integrations of the sensor measurements. Specifically, FIG. 4 illustrates a worksheet view in DASYLab™ of the various actions performed in one embodiment of the invention. Various icons as set forth in FIG. 4 illustrates particular actions which are performed. On the left side of the worksheet, an icon represents a data acquisition board 130 which may be part of the overall data acquisition hardware (see FIG. 3), shown with 8 outputs, 0–7, which match up with the inputs received from various of the sensors and other related inputs. The data acquisition signals are converted from analog to digital for further processing. Various inputs and outputs, in one embodiment of the invention, include: the signal 122 from the pressure transducer 120, the flow out signal 118 from flowmeter 94, the flow in signal 116 from the input flowmeter 81, the outflow chamber pressure 112 as determined by sensor 104, the inflow chamber pressure 114 as determined by sensor 106, an average of the measured outflow, an average of the measured inflow, and the EKG/ECG signal.

As will be understood by a person skilled in the art, the DASYLab worksheet uses icons to denote particular functions or steps. The icons in FIG. 4 will be referred to with respect to their function. Input 0 is a signal from the pressure transducer 120, such as a Codman™ pressure transducer. A pressure transducer, such as a Codman™ transducer inputs four leads into a strain gauge. Two of the leads are excitation leads for powering the transducer, and two are for the measured pressure signal. The output of the pressure transducer is in millivolts (mV). As such, a chart is created to compare the mV signal to pressure in mmHg. As illustrated in FIG. 4, the raw signal from the transducer is first directed into a filter 132, such as a low pass filter set at 100 Hz. The filter eliminates the extremely high noise but, at the same time, does not alias the signal. For an alternative design, the signal can be filtered at 10 Hz before analog/digital conversion. After the filter 132, the signal is scaled to mmHg using proper scaling, as indicated by icon 134. The signal then travels to a data record relay 136, which, when triggered, acts as a pathway for data to be recorded in the compute icon 137. The relay allows for data to be recorded over a given amount of time. The signal also goes to presentation icons, including a signal/time display 138 coupled to an appropriate chart icon 140, and to a differentiation icon 142, which is coupled through a filter 144, to an appropriate signal/time display 146 and chart or recorder 148. The pressure signal is also directed to a digital meter 150 and a graphing or display icon, and specifically, the pressure-volume display 152 for displaying pressure-volume loops. Such pressure-volume loops, as discussed further below, provide useful information regarding the operation of the explanted heart in accordance with the principles of the invention.

Inputs 1 and 2 are reflective of the measurements from the outflow meter 94 and inflow meter 81, respectively. The flow meters filter the raw signal at 10 Hz. The signals are then passed through the data acquisition board 130, and are illustrated by the $F_{OUT}$ conversion icon 154 and $F_{IN}$ conversion icon 156, where the signals are converted from raw voltage signals to flow signals in ml/sec. After the conversion, the signal goes to the data record relay 136 for recordation, and also the signal/time display 138 and associated chart or recorder 140. In that way, the measured flows might be visually tracked. The flow inputs are also directed to differentiation icon 142 and integration icon 158. Integration icon 158 integrates the signals as necessary with respect to the calculated volume inside the ventricle being measured. As noted above, the measured flow signals are utilized to add to or subtract from an absolute volume for making the relative volume determination within the system, such as for displaying pressure-volume loops. Differentiation icon 142 is reflective of the derivative of the measured flow signals, to find peaks and valleys of the flow. The differentiation icon 142, or step, utilizes filtering, such as from filter 144. The outputs from integration icon 158 are directed to add/subtract icon 160 which subtracts one integrated flow from the other for determining volume changes and setting starting points for the volume (found from echocardiograms) to display on the Pressure/Volume Display 152. The derived signals may then be displayed or recorded via icons 146, 148 and 152. The integrated volume signals are directed to display 152 for illustrating the pressure-volume loops. The outflow chamber pressure, such as the aortic chamber pressure for the left side of the heart, is indicated by input 3. The inflow chamber pressure is indicated at input 4 on the data acquisition board 130. The pressure transducers for the chambers may be Baxter™ disposable pressure transducers which include four pins for each transducer. Similar to the Codman™ pressure transducers noted above, there are two pins dedicated to the excitation of the transducer, and two pins dedicated to the signal measured by the transducer. The four pressure transducer inputs lead to a strain gauge, one for each transducer. The signals are then preferably filtered at a 100 Hz low pass filter (not shown in FIG. 4), and then directed to appropriate scaling at icon 162 and displayed with a chamber pressure digital meter 164. The flow signals measured from the flowmeters 81, 94 are also averaged. The signals from the flowmeters are pre-filtered and pre-averaged, and indicated by inputs 5 and 6 in FIG. 4. As discussed above with the flowmeters, the sensed voltage signals are converted to flow rate signals via conversion icons 154 and 156, and a suitable conversion factor, and then transferred to the data record relay 136 and into a digital meter 150. Input 7 is the EKG/ECG signal which comes from the surface of the heart, inputted by two leads into a pass-through module. The signal is appropriately filtered (icon 166), scaled (icon 168), and shown on a signal/time display, such as an ECG chart 170. An appropriate scale might be a 5 mV y-axis scale. As illustrated in FIG. 4, outputs from the differentiation icon 142 and integration icon 158 might also be stored or recorded via the data record relay.

In determining the pressure-volume relationship, the integration of the inflow and the outflow signals and the subtraction of the two integrals yields the change in ventricular volume. In one embodiment of the invention, a single chamber flow equation used to derive that concept is:

$$F_{IN} - F_{OUT} + \Delta V = 0$$

The initial volumes are estimated using ventricular algorithms with dimensions supplied by ultrasonic technology, as noted above.

Figure 5:
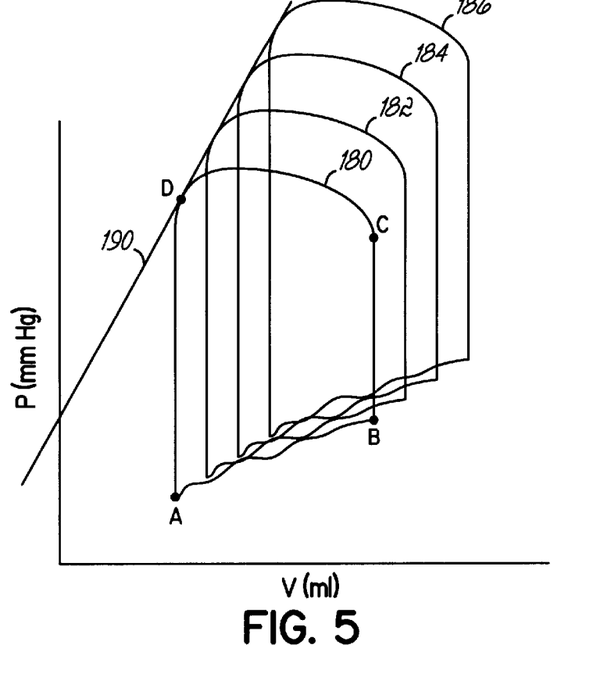
FIG. 5 is a graph of pressure-volume curves generated in accordance with one aspect of the present invention.

FIG. 5 illustrates a series of pressure-volume curves or loops which may be produced utilizing the present invention. From the multiple loops, function characteristics, such as the end systolic elastance may be determined, which is an indication of how a stressed heart will respond. From such curves, other characteristics may be determined as well, such as $E_{MAX}$.

Referring to FIG. 5, four loops, 180, 182, 184, and 186 are illustrated by way of example. Pressure is indicated in mmHg and volume in ml. On the loops, point A is indicative of the beginning diastole pressure which gradually rises to point B during diastole. At the beginning of the systolic phase of the cardiac cycle, the loop segment from point B to point C is indicative of the sharp rise in ventricular pressure during contraction of the ventricle. Point C is indicative of the ventricular outflow valve opening, and as the curve progresses from point C to point D, the ventricular volume is reduced as the pressure rises and then falls to point D, whereupon the ventricular valve outflow closes and there is a significant drop in pressure in the ventricle back to point A. The curves are cyclically repeated during the cardiac cycle.

Figure 6:
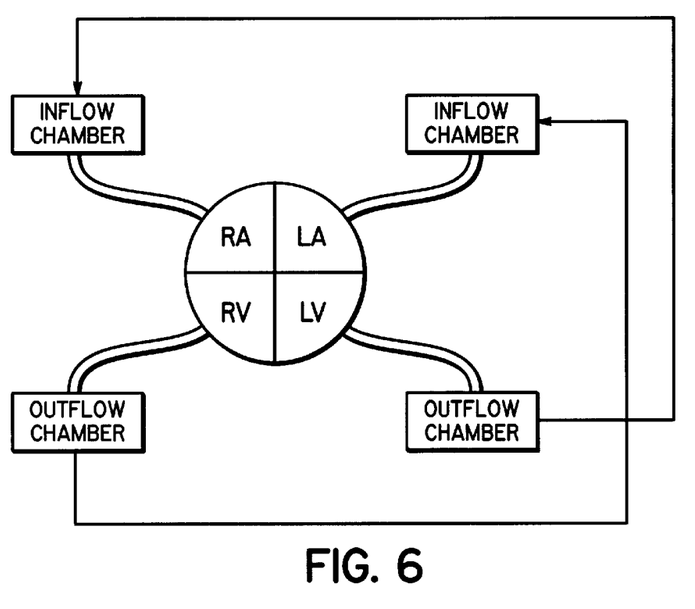
FIG. 6 is a schematic view of an embodiment of the system utilized for testing the entire heart.

By varying the baseline inflow pressure and the additional outflow pressure in the system, the curves 182, 184, and 186 are generated, and as shown in FIG. 6, will generally move to the right of the graph and upwardly. The ability of the heart to handle increased volume and pressures, and its ability to adapt, indicates its general health and operational characteristics. The tangent slope drawn generally through the points D of the curves 180–186 yields a particular slope. The slope of line 190 is referred to as the end systolic elastance. It is an indication of how a stressed heart will respond when pumping, and is a good indication of the overall health of the heart muscle and its operation. Other characteristics, such as $E_{MAX}$, may be determined from the curves illustrated in FIG. 5. In that way, the present invention provides a shape-independent methodology for determining the operational characteristics of the heart. Because flow rates are utilized in determining volume, and flow is generally shape independent, the present invention provides information that is generally shape independent.

The present invention has generally been described in an embodiment utilized to test the left side of the heart and the operation of the left ventricle. However, the present invention may be used to simultaneously study the entire heart; that is, the left and right sides, or the right side alone. Replication of many of the components of the single side system is required. Additional framework may be needed for suspending additional inflow and outflow chambers, meters, and necessary tubes for the circulation. With respect to the circuit to supply blood and/or other perfusate into the heart, additional inflow and outflow chambers are necessary. An outflow chamber from the left ventricle, which may be connected to the aorta or aortic valve ring, is connected via a throttle valve or resistor to an inflow chamber for the right ventricle, which may be connected to the right atrium or to the tricuspid valve ring. Similarly, the outflow chamber from the right ventricle, which is connected to the pulmonary artery, or pulmonic valve ring, is connected through a throttle valve or resistor to the inflow chamber for the left ventricle, which is connected to the left atrium or the mitral valve ring. The various sensors and data acquisition equipment associated with ventricle pressure, inflow and outflow chamber pressures, and fluid flow are also duplicated for the other side of the heart. The heart-lung subsystem also has additional connections to provide controllable inflow into a second inflow chamber. FIG. 6 shows a schematic diagram of the flow basics of the full heart system.

The present invention therefore provides the heart, or a portion of the heart, with a physiologic quantity and quality of coronary blood flow, with controllable inflow volumes (preload) so that pumping can take place. The system utilizes a controllable resistance to the outflow so that the required contractile force (afterload) may be monitored. Compliance is controlled so that the time-related pattern of pressure and flow in and out of the ventricles may be adjusted to approximate that observed in normal or pathologic physiologic conditions. The sensors provide data which is processed so that the volume contained in and pressure in the chambers of one or both of the ventricles may be monitored and related. The system provides significant advantages over existing systems for isolated heart perfusion. The particular advantage over balloon-based systems is that valvular function can be maintained in its near-normal state, or studied while being subjected to interventions suspected of having either a positive effect (i.e. facilitating valve closure or opening or lessening potentially harmful tensile stress on valve tissue) or negative effect (i.e. inhibiting closure, increasing mechanical stresses).

The present invention is also an improvement over existing systems by balancing heart wall pressures and eliminating the gravitational effects on the heart wall associated with existing systems. By generally reducing the dependency of the system on heart shape assumptions, the present invention provides a significant improvement over existing high-fidelity, high-frequency ventricular volume determination systems.

The system is relatively inexpensive to assemble and maintain, versus other systems which use a large number of sonocrystals associated with complex software. Furthermore, the present invention is less sensitive to sensor placement and takes less time to set up on the explanted heart. For example, the small number of sensors utilized may be readily positioned, as opposed to the large number of sonocrystals (e.g. 16–32) used by existing systems, such as one by Transonics, Ithaca, N.Y.

While the present invention has been illustrated by the description of the embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the invention in its broader aspects is not limited to the specific details representative apparatus and method, and illustrative examples shown and described. Accordingly, departures may be made from such details without departure from the spirit or scope of applicant's general inventive concept.

What is claimed is:

1. A system for studying a beating explanted heart comprising:
   a fluid inflow circuit configured for coupling to an explanted heart to direct fluid for flowing into a ventricle of the heart;
   a fluid outflow circuit configured for coupling to an explanted heart to direct fluid flowing out of the ventricle of the beating heart;
   a flow meter coupled with the inflow circuit for measuring the inflow rate of fluid into the heart ventricle;
   a flow meter coupled with the outflow circuit for measuring the outflow rate of fluid out of the heart ventricle;
   a processing system for converting the inflow and outflow rates into incremental volume changes in the volume of the heart ventricle and adding and subtracting the incremental volume changes from a relative volume of the heart ventricle to study volume changes in the explanted heart while it is beating.

2. The system of claim 1 further comprising a pressure sensor for coupling to the ventricle for measuring the ventricular pressure, the processing system operable for monitoring ventricular pressure changes and volume changes and graphing one versus the other for determining features of the heart.

3. The system of claim 1 wherein said inflow circuit comprises an inflow chamber for collecting fluid to be directed into the heart ventricle, the pressure in said inflow chamber being selectively adjustable for varying the pressure on fluid directed into the heart ventricle.

4. The system of claim 3 wherein said inflow circuit comprises a compliance chamber coupled to the inflow chamber and creating a variable pressure in the inflow chamber for varying the pressure of fluid flowing into the heart ventricle.

5. The system of claim 3 further comprising a pressure sensor coupled inside of the inflow chamber for sensing the pressure on fluid directed into the heart ventricle.

6. The system of claim 3 wherein said inflow circuit further comprises an overflow device coupled to the inflow chamber, the overflow device including a portion thereof which is vertically adjustable with respect to a level of fluid in the inflow chamber, for varying the pressure of the fluid flowing into the heart ventricle.

7. The system of claim 5 further comprising a resistor coupled between the inflow chamber and the overflow device for regulating the effect of the overflow device on the fluid pressure of the inflow chamber.

8. The system of claim 1 wherein said outflow circuit comprises an outflow chamber for collecting fluid flowing out of the heart ventricle, the pressure in said outflow chamber being selectively adjustable for varying the pressure of fluid flowing out of the heart ventricle.

9. The system of claim 8 wherein said outflow circuit comprises a compliance chamber coupled to the outflow chamber and creating a variable pressure in the outflow chamber for varying the pressure of fluid flowing from the heart ventricle.

10. The system of claim 9 wherein said outflow compliance chamber includes a flexible diaphragm positioned in the outflow chamber for interfacing with fluid in the outflow chamber.

11. The system of claim 8 wherein said outflow circuit comprises an outlet port coupled to the outflow chamber and a resistor coupled to the outlet port for controlling a flow of fluid out of the outlet port.

12. The system of claim 8 further comprising a pressure sensor coupled inside of the outflow chamber for sensing the pressure on fluid flowing out of the heart ventricle.

13. The system of claim 1 further comprising a collection apparatus configured for capturing fluid which may leak from the beating explanted heart, the collection apparatus being coupled to the inflow circuit to deliver the captured fluid for inflow to the heart ventricle.

14. The system of claim 1 wherein said inflow circuit includes a heart/lung machine for oxygenating and treating fluid flowing into the heart.

15. The system of claim 1 further comprising a circuit configured for coupling with coronary vessels of the explanted heart for delivering a fluid to the coronary vessels for keeping the heart alive.

16. A system for studying a beating explanted heart comprising:
   a fluid inflow circuit configured for coupling to an explanted heart to direct fluid for flowing into a ventricle of the heart;
   a fluid outflow circuit configured for coupling to an explanted heart to direct fluid flowing out of the ventricle of the beating heart;
   a collection apparatus configured for capturing fluid which may leak from the beating explanted heart, the collection apparatus comprising;
   a flexible bag configured to surround the heart and collect leaking fluid;
   a bath of fluid surrounding the bag to provide an outer pressure on the bag and heart therein to counteract fluid pressure inside of the heart.

17. The system of claim 16 wherein said flexible bag is suspended within the bath of fluid.

18. The system of claim 17 further comprising a float device coupled to the flexible bag for suspending the bag in the fluid bath.

19. The system of claim 16 wherein said flexible bag includes an outlet for draining fluid collected by the bag.

20. The system of claim 19 further comprising a rigid tube coupled with said outlet for enhancing the draining.

21. A method for studying a beating explanted heart comprising:
   directing, with an inflow circuit, a fluid for flowing into a ventricle of the heart;
   directing, with an outflow circuit, a fluid flowing out of the ventricle;
   measuring the inflow rate of fluid which will flow into the heart ventricle;
   measuring the outflow rate of fluid out of the heart ventricle;
   converting the inflow and outflow rates into incremental volume changes in the volume of the heart ventricle and adding and subtracting the incremental volume changes from a relative volume of the heart ventricle to study volume changes in the explanted heart while it is beating.

22. The method of claim 21 further comprising measuring the ventricular pressure in the ventricle.

23. The method of claim 22 further comprising monitoring ventricular pressure changes and volume changes and graphing one versus the other for determining features of the heart.

24. The method of claim 21 further comprising using an outflow chamber for collecting fluid flowing out of the heart ventricle and selectively varying the pressure in the outflow chamber for varying the pressure of fluid flowing out of the heart ventricle.

25. The method of claim 21 further comprising using an inflow chamber for collecting fluid to be directed into the heart ventricle and selectively varying the pressure in the inflow chamber for varying the pressure on fluid directed into the heart ventricle.

26. The method of claim 25 further comprising monitoring the pressure in the inflow chamber for determining the pressure on fluid being directed into the heart ventricle.

27. The method of claim 25 further comprising using an overflow device coupled to the inflow chamber for selectively varying the pressure of the fluid flowing into the heart ventricle.

28. The method of claim 27 further comprising vertically adjusting height of the overflow device with respect to a level of fluid in the inflow chamber for selectively varying the pressure.

29. The method of claim 25 further comprising using a compliance chamber coupled to the inflow chamber for selectively varying the pressure in the inflow chamber.

30. The method of claim 24 further comprising using a compliance chamber coupled to the inflow chamber for selectively varying the pressure in the inflow chamber.

31. The method of claim 30 wherein said outflow compliance chamber includes a flexible diaphragm positioned in the outflow chamber for interfacing with fluid in the outflow chamber.

32. The method of claim 24 wherein said outflow chamber comprises an outlet and a resistor coupled to the outlet for selectively controlling a flow of fluid out of the outlet port.

33. The method of claim 24 further comprising monitoring the pressure in the outflow chamber for determining the pressure on fluid flowing out of the heart ventricle.

34. The method of claim 21 further comprising capturing fluid, which may leak from the beating explanted heart, with a collection apparatus and directing the captured fluid for inflow to the heart ventricle.

35. A method for studying a beating explanted heart comprising:

directing, with an inflow circuit, fluid for flowing into a ventricle of the heart;

directing, with an outflow circuit, fluid flowing out of the ventricle;

capturing fluid, which may leak from the beating explanted heart, with a flexible collection apparatus configured to surround the heart;

surrounding the collection apparatus and heart with a bath of fluid and thereby providing an outer pressure on the collection apparatus and heart therein to counteract fluid pressure inside of the heart.

36. The method of claim 35 wherein said flexible collection apparatus is suspended within the bath of fluid.

37. The method of claim 36 further comprising coupling a float device to the flexible collection apparatus for suspending the bag in the fluid bath.

\* \* \* \* \*